United States Patent [19]

Mais et al.

[11] Patent Number: 5,391,767
[45] Date of Patent: Feb. 21, 1995

[54] PROCESS FOR THE PREPARATION OF ALKYLENE CARBONATES

[75] Inventors: Franz-Josef Mais, Düsseldorf; Hans-Josef Buysch, Krefeld; Christine Mendoza-Frohn, Erkrath; Alexander Klausener, Stolberg, all of Germany

[73] Assignee: Bayer Aktiengesellschaft, Leverkusen, Germany

[21] Appl. No.: 976,877

[22] Filed: Nov. 16, 1992

[30] Foreign Application Priority Data

Nov. 22, 1991 [DE] Germany .............................. 4138438
Apr. 2, 1992 [DE] Germany .............................. 4210943

[51] Int. Cl.$^6$ .......................................... C07D 317/18
[52] U.S. Cl. ..................................... 549/229; 549/230
[58] Field of Search ................................ 549/229, 230

[56] References Cited

U.S. PATENT DOCUMENTS 4,231,937  11/1980  Kao et al. ............................. 549/229
4,314,945  2/1982   McMullen et al. .................... 549/229
4,344,881  8/1982   Strege et al. ......................... 549/229

FOREIGN PATENT DOCUMENTS 2011402  12/1978  United Kingdom .

OTHER PUBLICATIONS

Chemical Abstracts, Dec. 10, 1973, No. 136527r.
Chemical Abstracts, BE (Belgium), No. 2855232.
Akio Baba, *The Chemical Society of Japan*, 1987, pp. 1552–1554.
Walter Dumler, Chem. Ber. 123, 1990, pp. 277–283.
Horst Kisch, Chem. Ber. 119, 1986, pp. 1090–1094.

*Primary Examiner*—C. Warren Ivy
*Assistant Examiner*—Raymond Covington
*Attorney, Agent, or Firm*—Sprung Horn Kramer & Woods

[57] ABSTRACT

Alkylene carbonates can be prepared by catalytic reaction of alkylene oxides with carbon dioxide, catalysts which can be regenerated of the formula $$a[MX]/b[ZnY_2] \qquad (III)$$

wherein

M denotes an alkali metal,
X and Y independently of one another denote chlorine, bromine or iodine and
a and b denote fractions or integers in a range from 0.001 to 2 being employed.

The catalysts (III) can be regenerated by treating with a halogen compound. The halogen compounds which can be used for this purpose belong to the group comprising hydrogen halides, inorganic and organic acid halides, interhalogen compounds and organic halides with mobile halogen.

19 Claims, No Drawings

PROCESS FOR THE PREPARATION OF ALKYLENE CARBONATES

BACKGROUND OF THE INVENTION

1. Field of the Invention

The present invention relates to a process for the preparation of alkylene carbonates by reaction of alkylene oxides with carbon dioxide in the presence of catalysts. Mixed catalysts of the formula $$a[MX]/b[ZnY_2] \quad \text{(III)}$$

which are mixed catalysts of alkali metal halides and zinc halides, are employed as the catalysts. These catalysts can be activated in addition by halogen compounds.

Alkylene carbonates, for example ethylene carbonate or propylene carbonate, are valuable intermediate products for the preparation of plastics, such as, for example, polycarbonates, or they are used as oxyalkylating agents for the synthesis of dyestuffs, plant protection agents or pharmaceuticals. Furthermore, they can be used as solvents, for example in fibre production.

2. Description of the Related Art

It is already known to react alkylene oxides with carbon dioxide in the presence of catalysts to give the cyclic alkylene carbonates. However, in order to achieve industrially adequate rates of reaction, high temperatures and high pressures are required for this process. This presents problems inasmuch as on the one hand the low molecular weight alkylene carbonates in particular arouse industrial interest, but on the other hand the alkylene oxides required for their preparation tend to decompose and therefore require particular safety equipment at high temperatures and under high pressures. High temperatures and high pressures furthermore cause a high expenditure on apparatus, in order to be able to maintain the desired reaction conditions. A large number of compounds have been disclosed to date as catalysts.

Such catalysts include ammonium, phosphonium and sulphonium salts (U.S. Pat. Nos. 2,773,070; 2,994,705; German Offenlegungsschrift 3,244,456), a combination of protic compounds and nitrogen-containing bases (German Offenlegungsschrift 2,611,087), arsonium halides (EP 180,387), tertiary phosphines (WO 84/03701), nitrogen bases (U.S. Pat. Nos. 3,535,341; 3,535,342) and alkali metal halides (BE 872,960). The reaction of alkylene oxides with carbon dioxide in the presence of a catalyst system of a metal chloride and tetraalkylammonium iodides is known from the general chemical literature (Chem. Ber. 119 (1986), 1090, and Chem. Ber. 123 (1990), 277). The reaction of alkylene oxides with carbon dioxide in the presence of catalyst systems comprising an organotin halide and a quaternary phosphonium halide furthermore is known (Bull. Chem. Soc. Japan 60 (1987), 1552). The procedure proposed in these publications comprises saturating a solution of the catalyst in the alkylene oxide with carbon dioxide and carrying out the reaction to give the alkylene carbonate in this manner under normal pressure and at a slightly elevated temperature. Because of the risk of decomposition described for the alkylene oxides, this procedure is unacceptable for safety reasons. The long reaction time (5 hours or more) and the relatively high amount of catalyst used, moreover, are unfavourable. It is furthermore unfavourable that these catalysts in general, as our own experiments have shown (Comparison Examples 3 and 7), soon lose their activity during recycling, which is to be aimed for industrially, and therefore disposal of a large amount of the inactive spent catalyst becomes necessary.

SUMMARY OF THE DESCRIPTION

A process has now been found for the preparation of alkylene carbonates of the formula

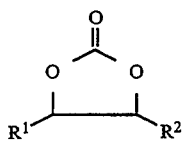

by reaction of alkylene oxides of the formula

wherein, in the formulae, $R^1$ and $R^2$ independently of one another denote hydrogen, substituted or unsubstituted $C_1$–$C_4$-alkyl, substituted or unsubstituted $C_2$–$C_4$-alkenyl or substituted or unsubstituted $C_6$–$C_{12}$-aryl and $R^1$ and $R^2$, together with the two three-membered ring C atoms, can denote a saturated carbocyclic ring having 5–8 ring members, with carbon dioxide in the presence of catalysts, which is characterised in that catalysts which can be activated of the formula $$a[MX]/b[ZnY_2] \quad \text{(III)}$$

wherein

M denotes an alkali metal, preferably Li, Na or K, especially preferably Na or K, X and Y independently of one another denote chlorine, bromine or iodine and a and b denote fractions or integers in a range from 0.001 to 2, are employed, whereby the activation can be carried out by the addition of a halogen compound of the formula $$R^3\text{—}Z$$

wherein

Z represents chlorine, bromine or iodine and $R^3$ denotes hydrogen, chlorine, bromine or iodine, the radical of an inorganic or organic acid halide, the radical or a benzyl, benzal or benzotrihalide, $C_4$–$C_8$-tert-alkyl, phenacyl, (meth)allyl or —CHR$^1$—CHR$^2$—OH, wherein $R^1$ and $R^2$ have the above meaning, and in the case where Z represents iodine, can also denote Cl$_3$ or Br$_3$, and whereby the reaction is carried out at a temperature of 40° to 250° C. and a molar ratio of alkylene oxide to CO$_2$ of 1:1–10.

DETAILED DESCRIPTION OF THE INVENTION $C_1$–$C_4$-Alkyl radicals can be straight-chain or branched, and substituted by halogen, aryl or alkoxy, for example methyl, ethyl, propyl, isopropyl, methoxymethyl, chloromethyl, benzyl and others; unsubstituted $C_1$–$C_4$-alkyl is preferred.

$C_2$–$C_4$-Alkenyl can be straight-chain or branched, and substituted by halogen, alkyl or aryl, for example vinyl, propenyl, 2-phenyl-vinyl, 2-chloro-vinyl and others; vinyl is preferred.

$C_6$–$C_{12}$-Aryl can be, for example, phenyl, naphthyl or biphenyl, preferably phenyl. Such aryl radicals can be substituted by alkyl, alkoxy, halogen or nitro. Examples of substituted aryl are: p-tolyl, o-tolyl, p-methoxyphenyl, p-nitrophenyl and p-chlorophenyl.

Examples which may be mentioned of a carbocyclic ring having 5–8 ring members which can be formed by $R^1$ and $R^2$ together with the two three-membered ring C atoms are: the cyclopentane ring, the cyclohexane ring and the cyclooctane ring.

Alkylene oxides in which the radicals $R^1$ and $R^2$ independently of one another denote hydrogen, methyl, ethyl, propyl, phenyl or chloromethyl are preferably employed in the process according to the invention.

Alkali metals M which may be mentioned are lithium, sodium, potassium, rubidium and caesium, preferably lithium, sodium and potassium, particularly preferably sodium and potassium.

Halogens X, Y and Z are, independently of one another, chlorine, bromine or iodine. X and Z are preferably bromine or iodine, particularly preferably bromine. Y is preferably chlorine or bromine, particularly preferably bromine.

It is preferable according to the invention for at least one of the halogens X and Y to denote bromine; particularly preferably, both X and Y denote bromine. Especially preferably, all three halogens X, Y and Z denote bromine. Halogen compounds of the formula (IV) which can in principle be employed in the manner according to the invention are those which contain a mobile halogen atom or halide ion and which do not fall under the constituents of the formula (III). In the case where $R^3$ denotes hydrogen, these are hydrogen chloride, hydrogen bromide, hydrogen iodide and their salts with nitrogen bases or with phosphorus bases, such as, for example, ammonium halides, phosphonium halides and pyridinium halides. In the cases where $R^3$ denotes chlorine, bromine or iodine, or $Cl_3$ or $Br_3$, the halogen compounds are the halogens $Cl_2$, $Br_2$ or $I_2$ and the interhalogen compounds, such as bromine chloride, iodine trichloride or iodine tribromide. In the case where $R^3$ represents the radical or an inorganic or organic acid halide, including phenacyl, the halogen compound (IV) includes compounds such as thionyl halides, sulphuryl halides, phosphorus trihalides, phosphorus pentahalides and phosphorus oxytrihalides, as important representatives of inorganic acid halides, and acetyl halides, propionyl halides, butyryl halides, benzoyl halides and benzoyl halides substituted by methyl, chlorine, bromine or hydroxyl, as important representatives of organic acid halides, and, for example, 2-haloethanol as an important example of a β-halogenoalkanol (halohydrines, Z—CHR$^1$—CHR$^2$—OH). In the case where $R^3$ denotes $C_4$–$C_8$-tert-alkyl, the halogen compound (IV) is a tert-butyl halide or tert-amyl halide. $R^3$ furthermore can denote (meth)allyl or the radical of a β-halogenoalkanol.

Further halohydrines for the inventive activation are, for example: 2-chloroethanol, 2-bromoethanol, 2-iodoethanol, 1-chloro-2-propanol, 2-chloro-1-propanol, 1-bromo-2-propanol, 2-bromo-1-propanol, 1-iodo-2-propanol, 2-iodo-1-propanol, 3-chloro-2-butanol, 3-bromo-2-butanol, 3-iodo-2-butanol, 1-bromo-2-butanol, 3-iodo-2-butanol, 1-bromo-2-butanol, 2-bromo-1-butanol, 2-chloro-2-phenylethanol, 2-bromo-2-phenylethanol, 2-iodo-2-phenylethanol, 2-chloro-1-phenylethanol, 2-bromo-1-phenylethanol, 2-iodo-1-phenylethanol, 1,3-dichloro-2-propanol, 2,3-dichloropropanol, 1-bromo-3-chloro-2-propanol, 2-bromo-3-chloropropanol, 1-iodo-3-chloro-2-propanol, 2-iodo-3-chloropropanol, etc.

In the case, that $R^3$ denotes $C_4$–$C_8$-tert.-alkyl, the halogen compound (IV) represents, e.g. tert.-butyl halide or tert.-amyl halide. Further, $R^3$ can represent (meth)allyl.

Preferably, halogen compounds of the formula $$R^{13}\text{—Z} \qquad (V)$$

in which
$R^{13}$ denotes hydrogen, $C_4$–$C_6$-tert-alkyl or —CHR$^{11}$—CHR$^{12}$—OH, wherein $R^{11}$ and $R^{12}$ independently of one another denote H, $CH_3$, $C_2H_5$ or phenyl, and
Z has the abovementioned scope of meaning,
are employed for the activation.

Especially preferably, halogen compounds of the formula $$R^{23}\text{—Br} \qquad (VI)$$

in which
$R^{23}$ denotes H or —CHR$^{11}$—CHR$^{12}$—OH, wherein $R^{11}$ and $R^{12}$ have the above meaning,
are employed for the activation.

The ratio of the fractions or integers a and b in the catalysts of the formula (III) is preferably in a range of a:b=20:1–1:5, particularly preferably 10:1–1:2, especially preferably 3:1–1:1.

A preferred form of the catalyst is also one in which the alkali metal halides and zinc halide are employed in a molar ratio of 2:1, or separately prepared complexes of the alkali metal halide and zinc halide are employed.

The carbon dioxide to be employed can be contaminated with inert gases, such as nitrogen, hydrogen, carbon monoxide and lower hydrocarbons, or can originate from natural sources or industrial waste gases.

The alkylene oxide to be employed can be either the industrially customary, pure alkylene oxide or a crude product containing an alkylene oxide, such as is obtained, for example, during oxygen oxidation of alkenes over metal-containing catalysts, such as, for example, silver catalysts.

The reaction pressure in the process according to the invention is in general an absolute reaction pressure of less than 30 bar, preferably less than 20 bar, particularly preferably less than 15 bar.

The reaction temperature is 40°–250° C., preferably 50°–200° C., particularly preferably 70°–170° C.

The molar ratio of alkylene oxide and carbon dioxide is in principle 1:1, but an excess of carbon dioxide is possible. Accordingly, according to the invention, the molar ratio of alkylene oxide to carbon dioxide is in the range from 1:1–10, and is preferably 1:1–3 and particularly preferably 1:1–1.5.

The amount of catalyst of the formula (III), based on the alkylene oxide in the reaction system, is 0.001–10% by weight, preferably 0.005–5% by weight, particularly preferably 0.01–2% by weight, especially preferably 0.02–1% by weight.

The reaction is carried out in the particular alkylene carbonate to be prepared as the reaction medium, that is to say in ethylene carbonate, if ethylene oxide is to be reacted with carbon dioxide, or in propylene carbonate, if propylene oxide is to be reacted with carbon dioxide.

It is of course also possible, for example, to react ethylene oxide with carbon dioxide in propylene carbonate; however, this variant is not preferred.

It is furthermore possible to dilute the reaction medium by substances which are inert under the reaction conditions. These are, for example, the solvents known to the expert, such as, for example, aliphatic hydrocarbons (decane, octadecane, decalin and others), aromatic hydrocarbons (benzene, toluene, xylene, mesitylene, tetrahydronaphthalene and others), cyclic amides (N-methylpyrrolidone, N-methyl-caprolactam and others) and ureas (N,N'-dimethyl-imidazolidin-2-one); furthermore, inert gases, such as nitrogen, hydrogen, argon and others, can also be used. The procedure without addition of such inert substances is preferred.

If dilution of the reaction medium with one of these solvents is chosen, it is furthermore possible for this solvent and the catalyst to be initially introduced into the reaction vessel as the reaction medium at the start of the reaction, without addition of the alkylene carbonate to be prepared. A reaction medium which is a mixture of this solvent and the alkylene carbonate is then formed in the course of the reaction due to the formation of the alkylene carbonate.

The process according to the invention can basically be carried out without any activating halogen compound. However, it is preferred that the catalyst which is obtained in the work-up of the reaction mixture is activated prior to its re-use by treatment with a halogen compound (IV). Such activation can be done as well before the first employment. This is especially important for the activation with halogen compounds of the formula

$$Z-CHR^1-CHR^2-OH,$$

wherein Z, $R^1$ and $R^2$ have the above meaning, and is very especially important for the activation with halohydrines which fall under the formula (VI).

The halohydrines can be added to the reaction mixture as such. However, they can also be created in the reaction mixture by the conversion of the inventively charged alkylene oxide of the formula (I) with hydrogen halide H—Z or with hydrogen halide releasing compounds or compound mixtures. It is preferred to add the halohydrines as such or to create them by introduction of hydrogen halide into the reaction mixture.

The amount of the halohydrine in the reaction mixture is arbitrary, in principle; even a very high excess of halohydrine does not disturb the inventive conversion. The amount of halogen contained in the halohydrine generally represents, relative to the amount of halogen in the employed compound of the formula (III), a molar ratio of Z to X+Y of 0.001 to 10, preferably 0.01 to 5, especially preferably 0.05 to 1, very especially preferably 0.1 to 0.5.

The amount of halogen compound (IV) to be employed according to the invention for the activation is, based on the sum of the compounds of the formula (III) present in the reaction mixture, 0.0001 to 100 times, preferably 0.0002 to 75 times, particularly preferably 0.0005 to 50 times, especially preferably 0.001 to 25 times this amount.

Any water introduced into the reaction medium does not interfere with the reaction according to the invention; it reacts with the alkylene carbonate to form carbon dioxide and the associated glycol derivative. However, it is preferable for all the starting substances to be employed with the low water content with which they are usually present in the chemical industry.

It is inventively preferred that in the reaction mixture the compounds of the formulae (I), (IV), (V) and (VI) carry the same radicals $R^1$ and the same radicals $R^2$, i.e., if, as an example, the feed compound of the formula (I) denotes ethylene oxide, 2-bromoethanol, as an example, is employed or if, as an example, the compound of the formula (I) denotes propylene oxide, (IV) represents a 2-halo-1-propanol or an 1-halo-2-propanol.

It is, however, as well possible according to the invention, that the feed compounds of the formula (I) and those of the formulae (IV), (V) and (VI) carry different radicals $R^1$ and different radicals among another.

The process according to the invention can be carried out in various embodiments:

One possibility comprises the discontinuous procedure in customary stirred vessels or bubble columns. In this case, alkylene oxide and carbon dioxide can be added until the vessel is full. The alkylene carbonate formed is then distilled off. Alkylene oxide and carbon dioxide are added again to the bottom product which remains. As the catalyst activity subsides, the halogen compound (IV) envisaged for the activation is added either before, during or after distillation of the alkylene carbonate formed.

It is equally possible also to carry out the activation of the catalyst (III) with the halogen compound (IV) only in a portion of the reaction medium or in a portion of the bottom product obtained after the alkylene carbonate has been distilled off. All the bottom products are the combined and recycled back to the reaction vessel for renewed use.

Another reaction variant relates to the preferred continuous reaction procedure. Possible reaction vessels here are the customary stirred kettles, bubble columns or cascades of kettles or bubble columns, which in turn can be arranged in various circuits, for example in series and/or parallel to one another. Carbon dioxide and the alkylene oxide are metered in continuously, and the alkylene carbonate is removed together with the catalyst contained therein. From this stream which has been removed, the alkylene carbonate is separated off from the catalyst system, according to the newly formed amount, for example by membranes or by distillation; all or some of the residue containing the catalyst is then recycled to the reaction vessel, or all or some is treated with the halogen compound (IV) envisaged for the activation.

In discontinuous or continuous performance, e.g. at the start of the reaction, a small amount of the alkylene carbonate to be produced is laid before together with the catalyst of the formula (III) but without the addition of halogen compounds, e.g. of halohydrines or halohydrine creating compounds. Thereafter the addition of the alkylene oxide and $CO_2$ is commenced. After the discontinuous addition has been stopped or with a continuously removed reaction stream, a low boiling fraction is taken off from the reaction mixture which contains halohydrine which was obtained during the reaction by side-reaction of the catalyst with the alkylene carbonate and protic compounds which are present initially or were contained in the fed alkylene oxide or $CO_2$. This low boiling fraction is recycled, together with the catalyst (III) containing sump, to the discontinuous or continuous reaction.

It is likewise inventively preferred, at a discontinuous or continuous performance and after the addition of a halohydrine to the start mixture comprising a small amount of alkylene carbonate and the catalyst of the formula (III) and after having carried out the conversion of alkylene oxide and $CO_2$, to take off a low boiling fraction within distilling off the newly produced alkylene carbonate and to recycle this low boiling fraction containing the originally fed and optionally to newly produced halohydrine.

Equally preferred is a continuous metering-in of halohydrine into a continuous conversion of alkylene oxide and $CO_2$, whereby the halohydrine can be prepared as well before the metering-in as also after the metering-in the reaction system from hydrogen halide and alkylene oxide or alkylene carbonate.

The process according to the invention is decidedly surprising in various respects. In the general chemical literature referred to, iodide-containing catalysts are expressly mentioned as being essential for a good catalytic action. It is thus completely unexpected that a mixture of simple alkali metal halides and zinc halide which also contains bromine has an excellent catalytic activity which exceeds that of the other systems already described, so that even under normal pressure, the reaction proceeds within a short time. It is furthermore surprising that precisely this mixture containing bromine can be recycled several times, and can then be activated after any loss in activity by addition of, for example, bromine compounds which do not belong to the catalyst system itself. Such reactivations of deactivated catalysts for reacting alkylene oxides with carbon dioxide have not previously been described.

The following examples illustrate the process according to the invention, but without limiting it to these.

EXAMPLE 1

700 g of ethylene carbonate, which contained 1.30 g of zinc bromide an 2.50 g of potassium iodide in dissolved form as catalysts, were introduced into a vertical tube 100 cm long and 3 cm in diameter provided with an oil heating jacket and, at the lower end, with a glass inlet frit, and the mixture was preheated to 120° C. 74 g of ethylene oxide and 82 g of carbon dioxide, as a gas mixture, were introduced uniformly through the base frit at this temperature in the course of 4 hours. The gas mixture was largely absorbed. After the end of the introduction of the gas, the mixture was drained into a flask and weighed. The weight increase which can be weighed in this manner was 146 g. Taking into account the loss during transfer, this corresponds to an almost quantitative conversion of the ethylene oxide. Analysis of the end product by gas chromatography showed that no by-products were formed. 160 g of ethylene carbonate were then distilled off from this batch under 18-22 mbar. The bottom product which remained was introduced into the bubble column again and gassed uniformly with 75 g of ethylene oxide and 83 g of $CO_2$ in the course of 4 hours. The weight increase was 148 g.

EXAMPLE 2

The process of Example 2 was repeated, except that here 2.14 g of zinc bromide and 1.97 g of sodium bromide were employed as catalysts. The amounts of gas passed in at 120° C. in the course of 4 hours were 72 g of ethylene oxide and 82 g of carbon dioxide. The weight increase which can be weighed after draining the mixture was 142 g. As in Example 1, 173 g of ethylene carbonate were distilled off and the bottom product was recycled. The amount passed in again was 75 g of ethylene oxide and 85 g of $CO_2$. The renewed weight increase was 146 g.

COMPARISON EXAMPLE 3

The process of Example I was repeated, except that here 1.3 g of zinc chloride and 5.0 g of tetrabutylammonium iodide were employed. 73 g of ethylene oxide and 77 g of $CO_2$ were passed in at 120° C. in the course of 4 hours. The increase was 122 g. After 155 g of ethylene carbonate had been distilled off under 20-22 mbar, the bottom product was gassed again with 70 g of ethylene oxide and 77 g of $CO_2$ at 120° C. The increase was only 33 g.

EXAMPLE 4

The process of Example 2 was repeated, except that here half the amount of the two catalysts, that is to say 1.07 g of zinc bromide and 0.98 g of sodium bromide, was employed. At the same time, the amount of gas passed in over a period of 4 hours was increased to such an extent that complete absorption of the ethylene oxide was no longer possible because of the short (about 70-80 cm) supernatant column of liquid. The amounts of gas passed in are shown in the table for Example 4. After determination of the weight, the amount (about 150-250 g) of ethylene carbonate formed was distilled off under a vacuum of 20-25 mbar and the bottom product which remained was introduced into the vertical tube again for recycling of the catalysts. After the catalysts had been recycled five times in this manner, and after distillation under 20-25 mbar and before reuse in the reaction tube, 4 g of HBr were blown uniformly into the distillation bottom product, which had a temperature of about 120° C., in the course of 15 minutes for reactivation. The activated bottom product was then initially introduced again into the reaction tube and recycled a further three times. Thereafter, 4 g of HBr were again passed into the bottom product after the distillation and before the renewed introduction. The bottom product was then introduced into the bubble column for the ninth recycling, that is to say its tenth use in total. The results are to be found in the table for Example 4.

TABLE for Example 4

| | Amounts of gas passed in | | Weight increase/g | Yield of EC based on EOX in % |
|---|---|---|---|---|
| | EOX/g | $CO_2$/g | | |
| Fresh batch | 124 | 140 | 206 | 83.1 |
| 1st Rc | 124 | 137 | 199 | 80.2 |
| 2nd Rc | 126 | 144 | 197 | 78.2 |
| 3rd Rc | 125 | 145 | 189 | 75.6 |
| 4th Rc | 120 | 146 | 165 | 68.8 |
| 5th Rc | 124 | 140 | 132 | 53.2 |
| Reactivation by HBr | | | | |
| 6th Rc | 120 | 143 | 175 | 72.9 |
| 7th Rc | 122 | 144 | 193 | 79.1 |
| 8th Rc | 125 | 140 | 189 | 75.6 |
| Reactivation by HBr | | | | |

TABLE for Example 4-continued

| | Amounts of gas passed in | | Weight increase/g | Yield of EC based on EOX in % |
|---|---|---|---|---|
| | EOX/g | CO$_2$/g | | |
| 9th Rc | 125 | 141 | 201 | 80.4 |

Reaction temperature: 120° C.
1.07 g of ZnBr$_2$/0.98 g of NaBr in 700 g of ethylene carbonate
Gases passed in for 4 hours
Rc: recycling
EOX: ethylene oxide
EC: ethylene carbonate

EXAMPLE 5

The process of Example 4 was repeated, except that here 1.07 g of zinc bromide and, instead of 0.98 g of sodium bromide, 0.70 g of sodium bromide were employed. The distillation of the ethylene carbonate content formed which was carried out after the weighing was undertaken in the same manner as in Example 4. Instead of HBr, 4 g of 2-bromoethanol were added to the bottom product, which had a temperature of about 100° C., after the fourth recycling. The results are to be found in the table for Example 5.

TABLE for Example 5

| | Amounts of gas passed in | | Weight increase/g | Yield of EC based on EOX in % |
|---|---|---|---|---|
| | EOX/g | CO$_2$/g | | |
| Fresh batch | 122 | 138 | 175 | 75.8 |
| 1st Rc | 120 | 140 | 176 | 73.3 |
| 2nd Rc | 122 | 140 | 159 | 65.2 |
| 4th Rc | 124 | 145 | 90 | 36.3 |
| Reactivation by 2-bromomethanol | | | | |
| 5th Rc | 120 | 140 | 134 | 55.8 |
| 6th Rc | 121 | 138 | 160 | 66.1 |
| 7th Rc | 119 | 138 | 158 | 66.4 |

Reaction temperature: 120° C.
1.07 g of ZnBr$_2$/0.98 g of NaBr in 700 g of ethylene carbonate
Gases passed in for 4 hours
Rc: recycling
EOX: ethylene oxide
EC: ethylene carbonate

EXAMPLE 6

The process of Example 4 was repeated, except that instead of zinc bromide, 0.65 g of zinc chloride and 0.98 g of sodium bromide were employed here. After the 1st recycling, reactivation was carried out by passing 2 g of HBr into the bottom product, which had a temperature of about 120° C. The results are to be found in the table for Example 6.

TABLE for Example 6

| | Amounts of gas passed in | | Weight increase/g | Yield of EC based on EOX in % |
|---|---|---|---|---|
| | EOX/g | CO$_2$/g | | |
| Fresh batch | 118 | 129 | 126 | 53.4 |
| 1st Rc | 120 | 122 | 64 | 26.7 |
| Reactivation by HBr | | | | |
| 2nd Rc | 115 | 133 | 116 | 50.4 |
| 3rd Rc | 118 | 128 | 132 | 55.9 |

Reaction temperature: 120° C.
0.65 g of ZnCl$_2$/0.98 g of NaBr in 700 g of ethylene carbonate
Gases passed in for 4 hours
Rc: recycling
EOX: ethylene oxide
EC: ethylene carbonate

COMPARISON EXAMPLE 7

The process of Example 4 was repeated, except that instead of the catalysts there, 0.67 g of zinc chloride and 2.55 g of tetrabutylammonium iodide were employed. After the first recycling, 3 g of HBr were passed into the bottom product, which had a temperature of about 110°–120° C. The result is to be found in the table for Comparison Example 7.

TABLE for Comparison Example 7

| | Amounts of gas passed in | | Weight increase/g | Yield of EC based on EOX in % |
|---|---|---|---|---|
| | EOX/g | CO$_2$/g | | |
| Fresh batch | 118 | 129 | 68 | 28.8 |
| 1st Rc | 120 | 133 | 8 | 3.3 |
| Reactivation by HBr | | | | |
| 2nd Rc | 115 | 125 | 1 | 0.4 |

Reaction temperature: 120° C.
0.67 g of ZnCl$_2$/2.55 g of tetrabutylammonium iodide in 700 g of ethylene carbonate
Gases passed in for 4 hours
Rc: recycling
EOX: ethylene oxide
EC: ethylene carbonate

EXAMPLE 8

The process of Example 4 was repeated, except that instead of the catalysts there, 1.07 g of zinc bromide and 1.12 g of potassium iodide were employed. After the second recycling, 2.5 g of 2-iodoethanol were added to the weighed reaction mixture employed for distilling off the ethylene carbonate formed, the portion formed (about 100–200 g) was then distilled off under 20 mbar and the bottom product which remained was introduced into the bubble column for recycling in the customary manner. The result is to be found in the table for Example 8.

TABLE for Example 8

| | Amounts of gas passed in | | Weight increase/g | Yield of EC based on EOX in % |
|---|---|---|---|---|
| | EOX/g | CO$_2$/g | | |
| Fresh batch | 120 | 129 | 158 | 65.8 |
| 1st Rc | 115 | 133 | 145 | 63.0 |
| Reactivation by HBr | | | | |
| 3rd Rc | 117 | 130 | 137 | 58.6 |
| 4th Rc | 112 | 119 | 139 | 62.1 |

Reaction temperature: 120° C.
1.07 g of zinc bromide/1.12 g of potassium iodide in 700 g of ethylene carbonate
Gases passed in for 4 hours
Rc: recycling
EOX: ethylene oxide
EC: ethylene carbonate

EXAMPLE 9

The process of Example 4 was repeated, except that here about 1–2 g of HBr in gaseous form were passed into the bottom product, which had a temperature of 100°–120° C., in the course of 2–3 minutes after each distillation of the ethylene carbonate formed, and the bottom product which remained was recycled to the bubble column. The result is to be found in the table for Example 9.

TABLE for Example 9

| | Amounts of gas passed in | | Weight increase/g | Yield of EC based on EOX in % |
|---|---|---|---|---|
| | EOX/g | CO$_2$/g | | |
| Fresh batch | 124 | 140 | 204 | 82.3 |
| Reactivation by HBr | | | | |
| 1st Rc | 126 | 138 | 203 | 80.6 |
| Reactivation by HBr | | | | |
| 2nd Rc | 130 | 139 | 203 | 78.1 |
| Reactivation by HBr | | | | |
| 3rd Rc | 122 | 144 | 198 | 81.2 |

TABLE for Example 9-continued

|  | Amounts of gas passed in | | Weight | Yield of EC based on |
|---|---|---|---|---|
|  | EOX/g | CO$_2$/g | increase/g | EOX in % |
| Reactivation by HBr | | | | |
| 4th Rc | 125 | 141 | 196 | 78.4 |
| Reactivation by HBr | | | | |
| 5th Rc | 127 | 142 | 202 | 79.5 |

Reaction temperature: 120° C.
1.07 g of ZnBr$_2$/0.98 g NaBr in 700 g of ethylene carbonate
Gases passed in for 4 hours
Rc: recycling
EOX: ethylene oxide
EC: ethylene carbonate

EXAMPLE 10

The process of Example 1 was repeated, except that instead of the catalysts there, 2.05 g of Na$_2$[ZnBr$_4$] were employed. 68 g of EOX and 80 g of CO$_2$ were passed in at 120° C. in the course of 4 hours. The increase was 133 g. After 149 g of ethylene carbonate had been distilled off under 20–25 mbar, the bottom product was employed again. 75 g of EOX and 82 g of CO$_2$ were passed in at 120° C. The weight increase was 147 g.

EXAMPLE 11

700 g of ethylene carbonate, 1.96 g of sodium bromide, 2.16 g of zinc bromide and 0.93 g of 2-bromoethanol were introduced into a vertical tube 110 cm long and 3 cm in diameter provided with an oil heating jacket and, at the lower end, with a gas inlet frit, and the mixture was preheated to 120° C. 78 g of ethylene oxide and 86 g of carbon dioxide, as a gas mixture, were introduced uniformly through the base frit at this temperature in the course of 4 hours. The gas mixture was largely absorbed. After the end of the introduction of the gas the mixture was drained into a flask and weighed. The weight increase which can be weighed in this manner was 153.5 g. Taking into account the loss during the transfer, this corresponds to a quantitative conversion of the ethylene oxide. The reaction product was introduced into a vacuum distillation apparatus, and 15.3 g of prerunnings were removed at a top temperature of 122° C. under a pressure of 20 to 22 mbar with the use of metalized 50 cm-Vigreux column. These prerunnings contained the 2-bromoethanol.

EXAMPLE 12

The process of Example 11 was repeated, except that here 0.46 g of 2-bromoethanol, 1.07 g of zinc bromide and 0.98 g of sodium bromide were employed. At the same time, the amount of gas passed in over a time of 4 hours was increased to such an extent that the complete absorption of the ethylene oxide was no longer possible because of the short (about 70–80 cm) supernatant column of liquid. The amounts of gas passed in are shown in the table to Example 12. After determination of the weight, the amount (about 200 g) of ethylene carbonate formed was distilled off under a vacuum of about 40 mbar and the bottom product which remained was introduced into the vertical tube again after the addition of 0.45 to 0.47 g of 2-bromoethanol. The result is to be found in the table for Example 12.

TABLE for Example 12

|  | Amounts of gas passed in | | Weight | Yield of EC based on |
|---|---|---|---|---|
|  | EOX/g | CO$_2$/g | increase/g | EOX in % |
| Fresh batch | 122 | 140 | 198 | 81.1 |
| 1st Rc | 124 | 138 | 196 | 79.0 |
| 2nd Rc | 125 | 140 | 196 | 78.4 |
| 3rd Rc | 122 | 140 | 193 | 79.1 |
| 4th Rc | 125 | 144 | 197 | 78.8 |
| 5th Rc | 123 | 141 | 194 | 78.9 |
| 6th Rc | 120 | 142 | 191 | 79.6 |
| 7th Rc | 118 | 140 | 186 | 78.8 |
| 8th Rc | 122 | 139 | 193 | 79.1 |
| 9th Rc | 121 | 140 | 194 | 80.1 |

Reaction temperature: 120° C.
Rc: recycling
EOX: ethylene oxide
EC: ethylene carbonate

EXAMPLE 13

The process of Example 12 was repeated, except that prior to the recycling of the remaining sump no 2-bromoethanol was added. The result is to be found in the table for Example 13.

TABLE for Example 13

|  | Amounts of gas passed in | | Weight | Yield of EC based on |
|---|---|---|---|---|
|  | EOX/g | CO$_2$/g | increase/g | EOX in % |
| Fresh batch | 123 | 139 | 201 | 81.7 |
| 1st Rc | 124 | 140 | 193 | 77.8 |
| 2nd Rc | 124 | 138 | 115 | 46.4 |
| 3rd Rc | 120 | 144 | 70 | 28.2 |
| 4th Rc | 122 | 151 | 57 | 23.4 |

Reaction temperature: 120° C.

EXAMPLE 14

The process of Example 12 was repeated, except that instead of a simple vacuum distillation now a first running (about 20 g) was removed at a top temperature of 136° C. under 40 mbar via a 50 cm-Vigreux column. Thereafter the newly formed amount of ethylene carbonate was likewise distilled via this column under 40 mbar. The remaining sump and the low boiling first running were introduced into the vertical tube in order to recycle the halohydrine and the catalysts. The result is to be found in the table for Example 14.

TABLE for Example 14

|  | Amounts of gas passed in | | Weight | Yield of EC based on |
|---|---|---|---|---|
|  | EOX/g | CO$_2$/g | increase/g | EOX in % |
| Fresh batch | 120 | 138 | 193 | 80.4 |
| 1st Rc | 118 | 140 | 188 | 79.6 |
| 2nd Rc | 122 | 142 | 192 | 78.7 |
| 3rd Rc | 120 | 138 | 188 | 78.3 |
| 4th Rc | 120 | 139 | 186 | 77.5 |
| 5th Rc | 119 | 142 | 185 | 77.7 |

Reaction temperature: 120° C.
Addition of 2-bromoethanol only to the fresh batch
Recycling of low boiling first running and remaining sump

EXAMPLE 15

The process of Example 12 was repeated, except that here 0.23 g of 2-bromoethanol, 0.41 g of 2-iodoethanol, 1.07 g of zinc bromide and 1.58 of potassium iodide were employed.

After distilling off of the formed ethylene carbonate, in each case 0.22 to 0.25 g of 2-bromoethanol and 0.40 to 0.43 g of 2-iodoethanol were added prior to the recycling of the remaining sump. The result is to be found in the table for Example 15.

TABLE for Example 15

| | Amounts of gas passed in | | Weight increase/g | Yield of EC based on EOX in % |
|---|---|---|---|---|
| | EOX/g | CO₂/g | | |
| Fresh batch | 122 | 140 | 200 | 82.0 |
| 1st Rc | 116 | 144 | 190 | 81.9 |
| 2nd Rc | 122 | 142 | 193 | 79.1 |
| 3rd Rc | 121 | 141 | 192 | 79.3 |
| 4th Rc | 123 | 145 | 194 | 78.9 |

Reaction temperature: 120° C.

EXAMPLE 16

The process of Example 12 was repeated, except that here 0.45 g of 2-bromoethanol, 0.65 g of zinc chloride and 0.99 g of sodium bromide were employed. After distilling off of the formed ethylene carbonate, in each case 0.43 to 0.46 g of 2-bromoethanol were added prior to the recycling of the remaining sump. The result is to be found in the table for Example 16.

TABLE for Example 16

| | Amounts of gas passed in | | Weight increase/g | Yield of EC based on EOX in % |
|---|---|---|---|---|
| | EOX/g | CO₂/g | | |
| Fresh batch | 123 | 143 | 192 | 78.0 |
| 1st Rc | 125 | 146 | 198 | 79.2 |
| 2nd Rc | 122 | 144 | 196 | 80.3 |
| 3rd Rc | 119 | 142 | 191 | 80.2 |
| 4th Rc | 120 | 144 | 191 | 79.5 |

Reaction temperature: 120° C.

What is claimed is:

1. A process for the preparation of an alkylene carbonate of the formula

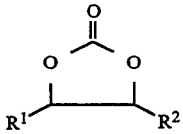

by reaction of an alkylene oxide of the formula

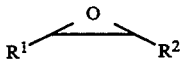

wherein, in the formulae,
  $R^1$ and $R^2$ independently of one another denote hydrogen, substituted or unsubstituted $C_1$–$C_4$-alkyl, substituted or unsubstituted $C_2$–$C_4$-alkenyl or substituted or unsubstituted $C_6$–$C_{12}$-aryl and
  $R^1$ and $R^2$, together with the two three-membered ring C atoms, can denote a saturated carbocyclic ring having 5–8 ring members,
with carbon dioxide in the presence of catalysts, wherein a catalyst which can be activated of the formula a[MX]/b[ZnY₂]

wherein
  M denotes an alkali metal,
  X and Y independently of one another denote chlorine, bromine or iodine, provided that at least one of X and Y is bromine, and
  a and b denote fractions or integers in a range from 0.001 to 2,
is employed in an amount of from 0.001–10% by weight, whereby the activation can be carried out by addition of a halogen compound of the formula

wherein
  Z represents chlorine, bromine or iodine and
  $R^3$ denotes hydrogen, chlorine, bromine or iodine, the radical of an inorganic or organic acid halide, the radical of a benzyl, benzal or benzotrihalide, $C_4$–$C_8$-tert-alkyl, phenacyl, (meth) allyl or —CHR¹—CHR²—OH wherein $R^1$ and $R^2$ have the above meaning, and in the case where Z represents iodine, can also denote Cl₃ or Br₃,
and whereby the reaction is carried out in the particular alkylene carbonate to be prepared, as the reaction medium, and at a temperature of 40° to 250° C. and a molar ratio of alkylene oxide to CO₂ of 1:1-10.

2. The process of claim 1, wherein in the catalyst M denotes Li, Na or K.

3. The process of claim Z, wherein in the catalyst M denotes Na or K.

4. The process of claim 1, which is carried out at 50° to 200° C.

5. The process of claim 4, which is carried out at 70° to 170° C.

6. The process of claim 1, which is carried out at a molar ratio of alkylene oxide to CO₂ of 1:1-3.

7. The process of claim 6, which is carried out at a molar ratio of alkylene oxide to CO₂ of 1:1-1.5.

8. The process of claim 1, wherein a halogen compound of the formula $R^{13}$—Z in which
  $R^{13}$ denotes hydrogen, $C_4$–$C_6$-tert-alkyl or —CHR¹¹—CHR¹²—OH, wherein $R^{11}$ and $R^{12}$ independently of one another denote H, CH₃, C₂H₅ or phenyl, and
  Z represents chlorine, bromine or iodine,
is employed for the activation.

9. The process of claim 1, wherein both halogens X and Y denote bromine.

10. The process of claim 9, wherein all the halogens X, Y and Z denote bromine.

11. The process of claim 1, wherein the activation of the catalyst by addition of the halogen compound $R^3$—Z is carried out prior to its recycling for a repeated use or already prior to its first use.

12. The process of claim 8, wherein a halogen compound of the formula $R^{23}$—Br, in which
  $R^{23}$ denotes hydrogen or —CHR¹¹—CHR¹²—OH wherein $R^{11}$ and $R^{12}$ independently of one another denote H, CH₃, C₂H₅ or phenyl,
is employed for the activation.

13. The process of claim 1, wherein in the case that a halohydrin of the formula

Z—CHR¹—CHR²—OH, in which
  $R^1$ and $R^2$ independently of one another denote hydrogen, substituted or unsubstituted $C_1$—$C_4$-alkyl, substituted or unsubstituted $C_2$-$C_4$-alkenyl or substituted or unsubstituted $C_6$-$C_{12}$-aryl and Z represents chlorine, bromine or iodine, is employed as the halogen compound, this halohydrine is employed as such or as a precursor from which such a halohydrine is produced in situ by the addition of hydrogen halide.

14. The process of claim 1, characterised in that the ratio of the integers or fractions a and b are in a range for a:b of 20:1 to 1:5.

15. The process of claim 1, which is carried out under an absolute reaction pressure of less than 30 bar.

16. The process of claim 15, which is carried out under a pressure of less than 20 bar.

17. The process of claim 16, which is carried out under a pressure of less than 15 bar.

18. The process of claim 1, wherein after the reaction and before or after the removal of the alkylene carbonate formed, the compound $R^3$—Z which activates the catalyst is added to the entire bottom product or to a part thereof, if $R^3$—Z is added before the alkylene carbonate formed is separated off, this separation is undertaken, and the bottom products are then recycled.

19. The process of claim 18, wherein in the case that an activating compound of the formula $$R^{23}\text{—Br},$$

in which $R^{23}$ denotes hydrogen or —$CHR^{11}$—$CHR^{12}$—OH, wherein $R^{11}$ and $R^{12}$ independently of one another denote H, $CH_3$, $C_2H_5$ or phenyl, is employed, in the work-up of the reaction mixture, prior to the distilling off of the alkylene carbonate, a low boiling fraction with the therein contained activating compound $R^{23}$—Br is removed and this low boiling fraction is recycled into the reaction, together with the distillation sump.

* * * * *